United States Patent [19]
Gillette et al.

[11] Patent Number: 5,584,824
[45] Date of Patent: Dec. 17, 1996

[54] CONTROLLED VACUUM CASSETTE IN OPHTHALMIC RETINAL SURGERY

[75] Inventors: Richard J. Gillette, County of Lincoln; James C. Easley, County of St. Charles, both of Mo.

[73] Assignee: Syntec, Inc., Winfield, Mo.

[21] Appl. No.: 255,659

[22] Filed: Jun. 8, 1994

[51] Int. Cl.⁶ ........................................... A61M 1/00
[52] U.S. Cl. ...................... 604/319; 604/320; 604/119
[58] Field of Search ................. 604/30, 34, 317–320, 604/118, 119, 133, 141, 149, 321, 323; 137/192–194

[56] References Cited

U.S. PATENT DOCUMENTS

| | | | |
|---|---|---|---|
| 3,768,478 | 10/1973 | Fertik | 604/320 |
| 4,475,904 | 10/1984 | Wang | 604/119 |
| 4,626,248 | 12/1986 | Scheller | 604/319 |
| 4,650,477 | 3/1987 | Johnson | 604/321 |
| 4,706,687 | 11/1987 | Rogers et al. | 128/752 |
| 4,758,238 | 7/1988 | Sundblom et al. | 604/319 |
| 4,773,897 | 9/1988 | Scheller et al. | 604/34 |
| 4,838,281 | 6/1989 | Rogers et al. | 128/752 |

*Primary Examiner*—Debra S. Brittingham
*Assistant Examiner*—Mark O. Polutta
*Attorney, Agent, or Firm*—Polster, Lieder, Woodruff & Lucchesi

[57] ABSTRACT

The invention relates to a cassette and vacuum aspiration collection system for ophthalmic surgery. The cassette comprises two parts under vacuum where the smaller part discharges into the larger part and the vacuum provided to both parts is provided by a single unit. The vacuum control system has improved response to the user's demand.

11 Claims, 2 Drawing Sheets

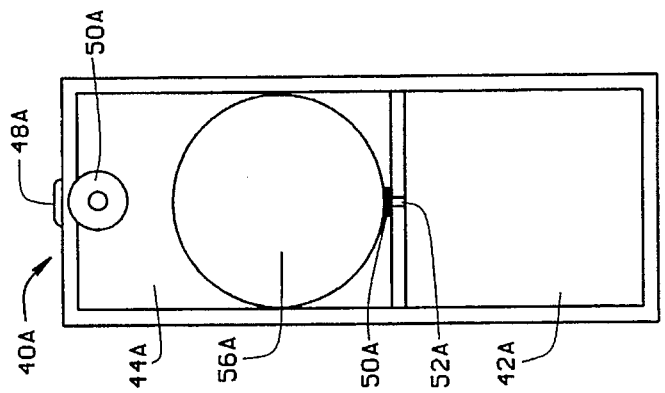
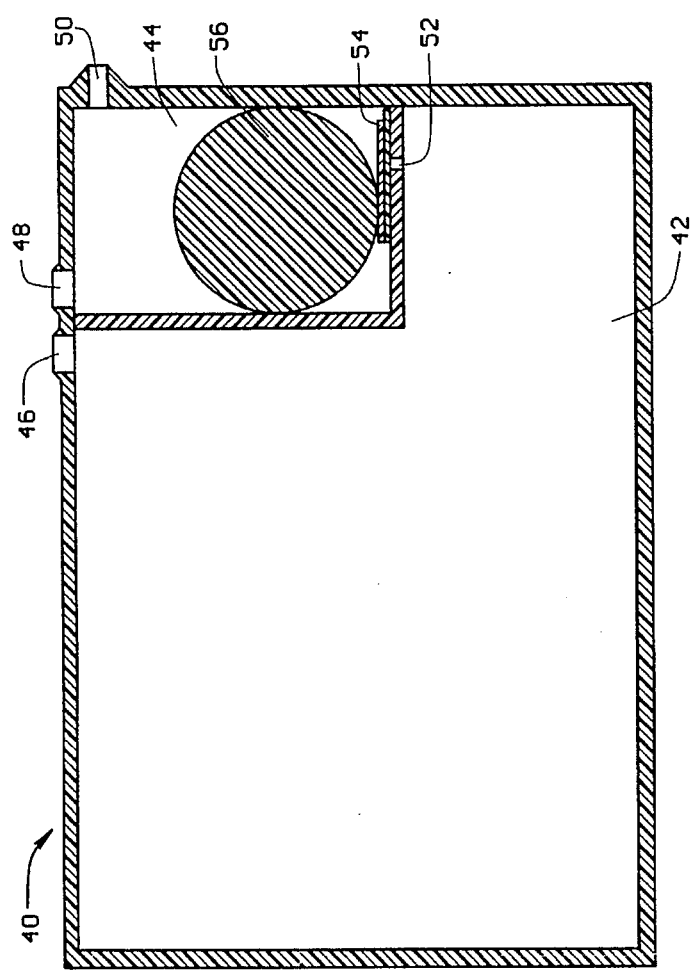
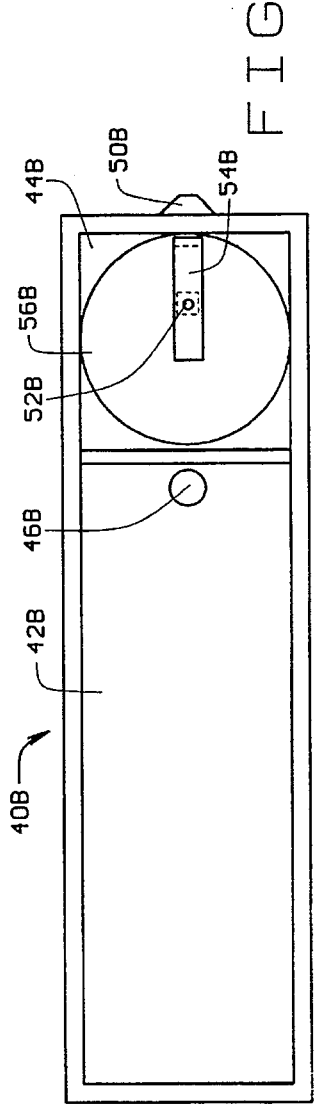

CONTROLLED VACUUM CASSETTE IN OPHTHALMIC RETINAL SURGERY

FIELD OF THE INVENTION

The present invention relates to an apparatus for controlling vacuum in ophthalmic surgery. More particularly, the invention relates to a cassette and to a vacuum aspiration collection system containing the cassette. The cassette provides rapid response to the vacuum requirements.

BACKGROUND OF THE INVENTION

In ophthalmic retinal surgery there exists a need for controlled vacuum. This vacuum can be used to remove debris, fluids or gases from the eye. It may also be used to manipulate membranes or other structures. When a vacuum is used to perform various tasks during surgery, different vacuum levels are required. Ideally, a surgeon is allowed to choose the appropriate vacuum level as the requirements change. This is normally accomplished through the use of a foot pedal. As the foot pedal is depressed, the vacuum level is increased proportionally. Most desirably, the vacuum level should track very closely to commands from the foot pedal or other control device.

Another requirement of the vacuum control system is to quickly and easily dispose of the aspirant (fluid or material suctioned or removed from the surgical process). Usually this is accomplished by flowing the aspirant into a bottle, bag or other container which generally has a volume of about 250 cc or more. The container is desirably transparent in order to aid in observation of the contents. These containers are commonly referred to as aspiration cassettes or aspiration bags. The aspiration cassette (cassette) should have enough capacity to capture the entire aspirant generated during a surgical procedure without overflowing or releasing fluids into the rest of the vacuum system.

Desirably, the cassette is simple to operate and inexpensive to manufacture as well as reliable during use. Since the vacuum control system is used for surgery, the system should operate quietly so as not to be a distraction.

In the past, various systems have been used to provide the vacuum control. One method uses a peristaltic pump. The aspiration line is connected to the surgical instrument at one end, runs through the pump and then empties into a bag or container at the other end. The vacuum is pulsed because of the roller action. It is difficult to measure and control the actual vacuum in the aspiration line without invading the line. The traditional method for changing the vacuum is to change the speed that the roller turns. It is difficult to control the pump speed rapidly enough to vary the vacuum synchronous with the changing requirements.

Most methods utilize a vacuum pump for a vacuum source. The vacuum is modulated by changing the pump speed or by using a variable orifice control for the vacuum. The vacuum is usually applied to a container to capture the aspirant. An aspiration line is connected to the container at one end and the surgical instrument at the other. In order for the vacuum to be responsive to the surgical requirements, the vacuum pump must evacuate the container volume. If the vacuum pump is sized so as to evacuate the volume quickly, the pump is prohibitively large. The most popular current method applies a Venturi as the vacuum source. This method requires a separate air source generally supplied by a tank of compressed nitrogen. In order to change the vacuum being generated, either the pressure to the Venturi can be modulated or the vacuum generated can be changed. As is the case with the vacuum pump, the vacuum is routed to a container. Since the system uses a separate pressure source, a change in vacuum is effected more quickly than with a vacuum pump, but the response time is still less than ideal. A higher flow Venturi could be used, but the increased input flow is objectionable. An internal air compressor could be included in the system, but like the vacuum pump, the compressor would be prohibitively large.

In order to increase vacuum responsiveness without increasing input air flow requirements, one system uses a cassette that is comprised of two containers. A smaller container has aspirant and controlled vacuum by a Venturi routed to it. When the system senses that the smaller container is almost full, it temporarily interrupts the vacuum. It then applies vacuum from a second Venturi to the larger container. This causes the aspirant to transfer from the smaller container into the larger one. Although this method works better than its forerunners, the vacuum response is still slower than desired, a separate pressure source is required, and the cassette mechanism is complex.

Objects to be met in the development of a new system would include: deposit of aspirant with no interruption of vacuum level; quick response of vacuum level when needed; sufficient containment space for aspirant; simple and inexpensive parts; and, requirement of only one vacuum source.

SUMMARY OF THE INVENTION

The present invention provides a surgical cassette which has two interconnected chambers. The first chamber is the smaller and has a volume of at least about 25 cc. The second chamber has a volume at least about four times that of the first chamber. The chambers are interconnected by a controlled orifice. When the chambers are under vacuum, the level of vacuum in the first chamber is at least about 40 mm Hg absolute less than in the second chamber thereby assisting the passage of aspirant through the controlled orifice from the first chamber to the second larger chamber. The vacuum level in the first chamber is substantially uninterrupted when the aspirant is passed from the first chamber to the second chamber.

The present invention further provides a surgical suction control system for aspirating and cutting tissue comprising:

(a) a cassette having two interconnected chambers, a first chamber having a volume of at least about 25 cc and a second chamber having a volume at least about four times that of the first chamber, the chambers being interconnected by a controlled orifice whereby aspirant is passed from the first chamber to the second chamber;

(b) a vacuum pump connected to the second chamber to provide a vacuum of at least about 400 mm Hg absolute, the vacuum being maintained at a predetermined level;

(c) a vacuum conduit interconnecting the second chamber to the first chamber to provide a vacuum means for the first chamber;

(d) a vacuum regulator to regulate the vacuum in the first chamber to a level selected by an external control means, the level being at least about 40 mm Hg absolute less than the vacuum level of the second chamber; and (e) an aspiration line connected from the first chamber to a surgical device.

More specifically, the present invention provides a cassette with two chambers which require only a small vacuum pump. The pump is capable of generating a negative pressure of at least 550 mm Hg absolute and is capable of flowing aspirant at 2.5 liters/minute at 400 mm Hg. The system is small enough and light enough in weight to allow insulation from sound without using too much space.

Preferably, the large chamber has a volume of about 500 cc. The vacuum generated by the vacuum pump generally is routed to the large chamber directly. The pump is allowed to run continuously, thus building a vacuum of at least 550 mm Hg in the chamber when the vacuum system is at idle. The small chamber preferably has an available volume of about 50 cc. A channel or hole from about 0.6 mm to about 2.0 mm in diameter connects the two chambers. In a preferred embodiment, a float, about 37.5 mm in diameter, is in the small chamber. The float is attached to a flap-type valve that occludes the hole to the larger chamber. Vacuum is routed from the large chamber to a variable orifice or a vacuum regulator. The regulated vacuum is then routed to the smaller chamber. The vacuum is regulated to a maximum value of about 400 mm Hg in the smaller chamber. In use, there should be at least 40 mm Hg greater vacuum in the larger chamber than in the smaller chamber. A connection for an aspiration line is provided in the smaller chamber.

BRIEF DESCRIPTION OF THE DRAWINGS

FIG. 2 is a front elevational view of another embodiment of the present invention;

FIG. 2A is a side elevational view of FIG. 2; and

FIG. 2B is a bottom view of FIG. 2.

DETAILED DESCRIPTION OF THE INVENTION

Figure 1:
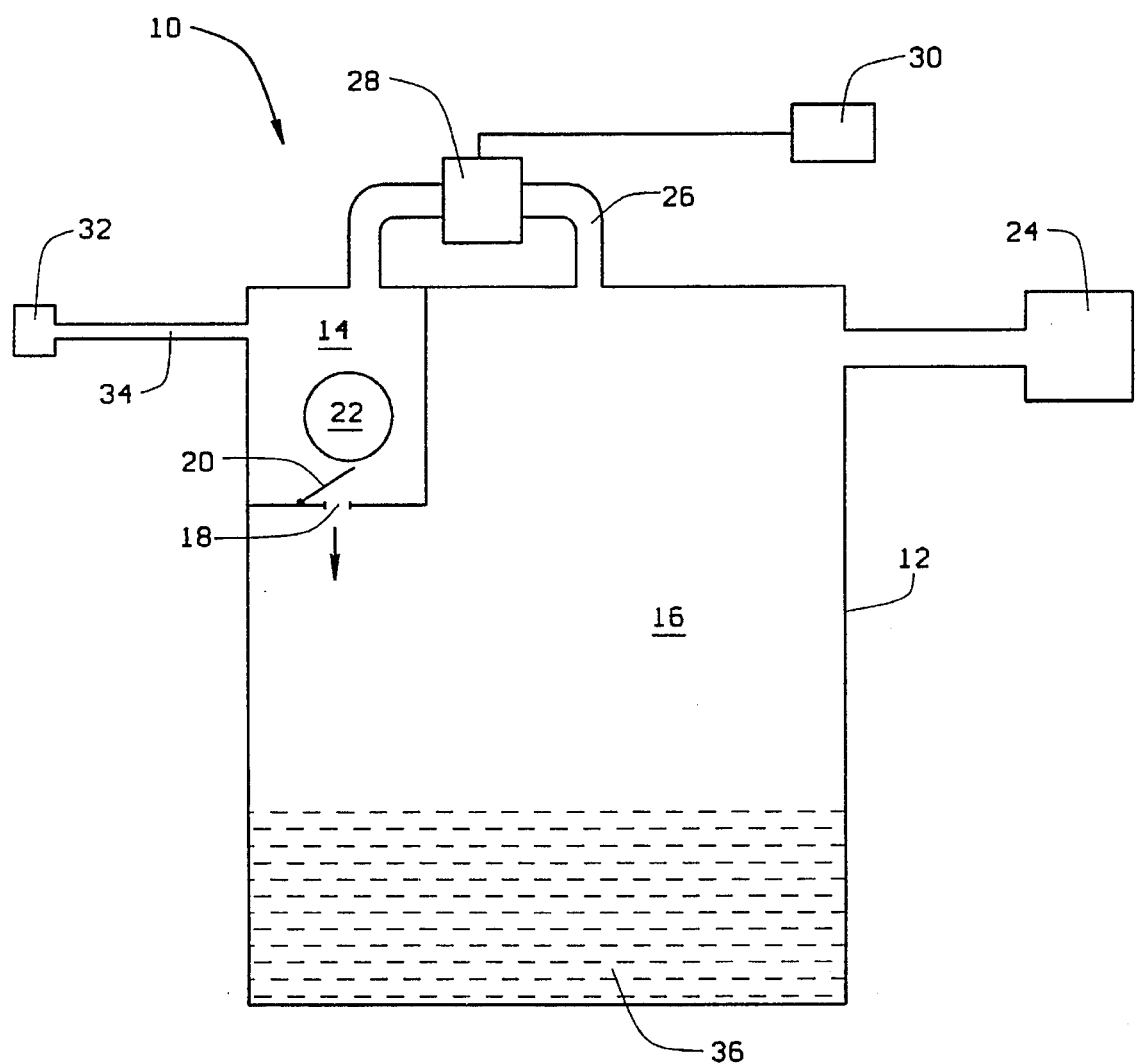
FIG. 1 is a front elevational view of one embodiment of the present invention.

With respect to FIG. 1, a vacuum aspiration collection system 10 has a cassette 12 with a large chamber 16 and a small chamber 14. There is an orifice 18 between the small chamber 14 and the large chamber 16. The orifice is closed when the flap valve 20 covers the orifice 18. The valve 20 is controlled by a float 22 so that when the aspirant flowing from the aspirant line 34 fills the chamber 14 part way, the float 22 opens the valve 20. A vacuum is created in the chamber 16 by the vacuum pump 24. A conduit 26 from the chamber 16 extends to the chamber 14 through a regulator 28 having a variable orifice. The regulator 28 controls the amount of vacuum in the small chamber 14. A foot pedal 30 connected to the regulator 28, allows the surgeon to control the vacuum within a predetermined range in the small chamber 14. The surgical device 32 is connected to the small chamber 14 through an aspiration line 34. As the aspirant comes from the surgical device 32, it is drawn through the aspirant line 34 into the small chamber 14. As the level of aspirant rises in the small chamber 14, the float 22 rises and opens the flap valve 20 whereupon the aspirant exits the small chamber 14 through the orifice 18 into the large chamber 16 where the vacuum is greater than that in the small chamber 14. The aspirant 36 is collected in the large chamber 16.

With respect to FIGS. 2, 2A and 2B, the numbers in FIGS. 2A and 2B correspond to the numbers in FIG. 2. With respect to FIG. 2, a cassette 40 is depicted having a small chamber 44 contained within a large chamber 42. The large chamber 42 has an exit port 46 where a conduit is affixed leading to a vacuum pump (not shown) and a vacuum regulator (not shown) and thence to an exit port 48 of the small chamber 44. The small chamber 44 has an orifice 52 leading to the large chamber 42. The orifice 52 is covered by a valve 54, which valve is controlled by a float 56. The small chamber 44 also has a second exit port 50 where an aspiration line (not shown) is attached.

When operating, the system starts with the larger chamber at its maximum vacuum and the smaller chamber at atmospheric pressure. The flap valve between the two chambers is closed. When the command comes from the foot pedal for a specific vacuum, the variable orifice opens. Because the larger chamber acts as an accumulator, air exits the smaller chamber at a rate controlled and limited by the orifice and tubing size linking the larger and smaller chambers. The vacuum in the smaller chamber reaches the desired level very rapidly quickly approaching the vacuum of the larger chamber. When the vacuum in the smaller chamber reaches the desired level, the regulator controls the orifice size to maintain or change the vacuum level as required by the surgeon. If it becomes necessary to lessen the vacuum level, the orifice is equipped to adjust the level using atmospheric pressure to achieve the desired level.

As aspirant enters the smaller chamber, the fluid level will rise on the float. Because there is more vacuum i.e., a lower negative pressure, in the larger chamber at all times, a force is applied which holds the valve closed between the two chambers. At some point, the aspirant level will rise enough to overcome the closing force on the valve. The float will rise a small amount, opening the hole between the two chambers. The aspirant will be drawn through the hole because of the higher vacuum level in the larger chamber. Shortly after the valve opens, the aspirant level will drop sufficiently in the small chamber and the valve will close.

The present invention provides no interruption of vacuum to the surgical device and little, if any variance in vacuum level during aspiration of the aspirant from the smaller chamber to the larger chamber. Furthermore, continuous aspiration is available. The vacuum response is quick and accurate allowing rapid changes to assist the surgeon. The aspirant container is large enough to allow lengthy surgery to take place without interruption. The system is comprised of simple and inexpensive parts making the system easy to clean and maintain. Furthermore, only one vacuum pump is required.

We claim:

1. A surgical cassette and aspiration system comprising:

(a) a first chamber having a first volume;

(b) a second chamber having a second volume, the volume of said second chamber being at least about four times that of the first chamber, the first chamber being contained within the second chamber, the chambers being interconnected by a controlled orifice;

(c) a vacuum source connected to the second chamber to provide a vacuum of at least about 400 mm Hg gauge, the vacuum being maintained at a predetermined level; and (d) a vacuum means for applying the vacuum of the second chamber to the first chamber such that the vacuum of the first chamber quickly approaches the vacuum of the second chamber, the controlled orifice permitting passage of aspirant through the controlled orifice from the first chamber to the second chamber substantially without interruption of the vacuum level in the first chamber.

2. The surgical cassette and aspiration system of claim 1 wherein the controlled orifice is controlled by a valve.

3. The surgical cassette and aspiration system of claim 2 wherein the valve is a float valve.

4. The surgical cassette and aspiration system of claim 3 wherein the first chamber has a volume of about 50 cc and the second chamber has a volume of about 500 cc.

5. The surgical cassette and aspiration system of claim 4 wherein the vacuum of the second chamber reaches a level of at least about 550 mm Hg absolute and the vacuum of the first chamber does not exceed a level of about 400 mm Hg absolute.

6. The surgical cassette and aspiration system of claim 1 including a vacuum conduit interconnecting the second chamber to the first chamber to provide the vacuum means for the first chamber; a vacuum regulator to regulate the vacuum in the first chamber to a level selected by an external control means, the level being at least about 40 mm Hg absolute less than the vacuum level of the second chamber; and an aspiration line connected from the first chamber to a surgical device.

7. The surgical cassette and aspiration system of claim 6 wherein the first chamber of the cassette has a volume of about 50 cc and the second chamber of the cassette has a volume of about 500 cc.

8. The surgical cassette and aspiration system of claim 6 wherein the controlled orifice is a hole whose opening and closing is controlled by a valve.

9. The surgical cassette and aspiration system of claim 8 wherein the valve is controlled by a float.

10. The surgical cassette and aspiration system of claim 6 wherein the vacuum level in the first chamber does not exceed about 400 mm Hg gauge and the level of the vacuum in the second chamber reaches a level of at least about 550 mm Hg gauge.

11. The surgical cassette and aspiration system of claim 6 wherein the first chamber of the cassette has a volume of about 50 cc and the second chamber of the cassette has a volume of about 500 cc and the vacuum level in the first chamber does not exceed about 500 mm Hg gauge and the level of the vacuum in the second chamber reaches a level of at least about 550 mm Hg gauge.

* * * * *